United States Patent [19]

Kondo et al.

[11] Patent Number: 5,554,526

[45] Date of Patent: Sep. 10, 1996

[54] HUMAN PARAINFLUENZA VIRUS TYPE 4A FUSION PROTEIN AND GENE CODING FOR THE SAME

[75] Inventors: Kunio Kondo, Ushiku; Mitsuo Kawano; Yasuhiko Ito, both of Tsu, all of Japan

[73] Assignee: Fujikura Kasei Co., Ltd., Tokyo, Japan

[21] Appl. No.: 321,587

[22] Filed: Oct. 11, 1994

Related U.S. Application Data

[63] Continuation of Ser. No. 915,826, filed as PCT/JP91/01402, Oct. 15, 1991 published as WO92/09693, Jan. 11, 1992, abandoned.

[30] Foreign Application Priority Data

Nov. 29, 1990 [JP] Japan ..................... 2-325171

[51] Int. Cl.$^6$ .................. C12N 5/00; C12N 15/00; C12Q 1/68; C07H 17/00
[52] U.S. Cl. .................. 435/240.1; 435/320.1; 435/6; 536/23.72; 536/24.3
[58] Field of Search .................. 536/23.72, 24.3; 435/69.1, 320.1, 240.1

[56] References Cited

U.S. PATENT DOCUMENTS

| | | | |
|---|---|---|---|
| 4,743,553 | 5/1988 | Rice | 435/253 |
| 4,790,987 | 12/1988 | Compans et al. | 424/89 |
| 5,169,628 | 12/1992 | Wathen | 424/89 |

FOREIGN PATENT DOCUMENTS 9002566  3/1990  WIPO .

OTHER PUBLICATIONS

Komada et al., Virology, "Virus–Specific Polypeptides of Human Parainfluenza Virus Type 4 and Their Synthesis in Infected Cells", vol. 171, No. 1, Jul. 1989, pp. 254–259.

Ray et al., Virus Research, "Expression of The Fusion Glycoprotein of Human Parainfluenza Type 3 Virus in Insect Cells By A Recombinant Baculovirus and Analysis of Its Immunogenic Property", vol. 12, No. 2, Feb. 1989, pp. 169–180.

Paterson et al., Proceedings of the National Academy of Sciences of USA, "Fusion Protein of The Paramyxovirus Simian Virus 5: Nucleotide Sequence of mRNA Predicts a Highly Hydrophobic Glycoprotein", vol. 81, Nov. 1984, pp. 6706–6710.

Waxham, M. N., et al., Virology, vol. 159, pp. 381–388, Aug., 1987.

Landry, M. L., et al., Clinics in Laboratory Medicine, vol. 5, No. 3, pp. 513–529, Sep., 1985.

Ito, Y., et al., Journal of General Virology, vol. 68, pp. 1289–1297, May, 1987.

Komada, H., et al., Virology, vol. 171, pp. 254–259, Jul., 1989.

Olmsted, R. A., et al., Proceedings of the National Academy of Sciences (USA), vol. 83, pp. 7462–7466, Oct., 1986.

Hall, S. L., et al., Vaccine, vol. 9, pp. 659–667, Sep., 1991.

Kondo, K., et al., Virology, vol. 174, pp. 1–8, Jan., 1990.

Bando, H., et al., Virology, vol. 175, pp. 307–312, Mar., 1990.

Primary Examiner—Robert A. Wax
Assistant Examiner—K. Cochrane Carlson
Attorney, Agent, or Firm—Wenderoth Lind & Ponack

[57] ABSTRACT

Human parainfluenza virus type 4A (PIV-4A) fusion protein and a gene coding for PIV-4A fusion protein are disclosed. This gene is obtained from a library derived from mRNA obtained from cells infected with PIV-4A and can be utilized for diagnosis of PIV-4A infective diseases. The PIV-4A fusion protein which is an expression product of this gene can be utilized for the production of an anti-PIV-4A antigen or vaccine.

10 Claims, 8 Drawing Sheets

0

CCACCATCAAGCACACAGCTCCAAATCCTGAGGTGATCAA

40

CACCCTTCGAATTCAATTCCATCACCAAAGAATCCAACAT

80

GGGTGTCAAAGGTTTATCTTTAATTATGATTGGTTATTA

120

ATCTCACCAATTACCAATCTGGATATAACTCATTTAATGA

160

ATCTAGGAACGGTACCGACTGCAATTAGATCTCTAGTTTA

200

CTACACTTATACCAAACCATCTTATCTCACTGTAGATTTG

240

ATTCCCAATTTGAAGAATCTGGACCAAAATTGCAATTACT

280

CAAGCTTAAACTACTACAACAAAACTGCACTAAGCCTAAT

320

TCAACCAATTGCAGATAACATCAATCGCCTTACAAAGCCC

360

ATCACAAGCTCAGAAATTCAAAGTCGTTTCTTTGGGGCAG

400

TCATAGGTACAATTGCTCTTGGTGTAGCCACCGCTGCACA

440

AGTTACAGCAGCAATCGGTCTAGCAAAAGCTCAAGAAAAT

GCAAAACTTATACTAACTCTCAAAAAGCTGCGACAGAAA

520

CAAATGAGGCAGTTCGAGATCTTGCAAACTCTAATAAAAT

560

TGTAGTAAAATGATATCAGCAATTCAAAATCAAATAAAC

600

ACTATTATTCTTCCTGCTATAGATCAGATTAATTGTCAAA

640

TTAAAGACCTACAAGTTGCCAATATTTTAAATTTGTACCT

680

AACAGAGATAACGACTGTTTTCCACAACCAATTGACCAAT

720

CCTGCATTAGAGTCAATTAGCATCAGCTCTCAAAGCTCTA

760

GGACTACCTACCTACCAGAAGTGTCATCTAAATTAGATTT

800

AAACAACATCTCGGCAGCTTCAGTGATGGCATCCGGCTTA

840

ATTAAGGACAGATAATTGCAGTTGATATACCGACTATGA

880

CACTAGTATTGATGGTCCAAATACCGAGTATATCCCCTTT

920

AAGACAAGCAAAGATAATAGATCTAACTTCTATAACAATT

CACACAAATAGCCAAGAAGTACAGGCTGTAGTACCGGCTA

1000

GGTTTCTCGAGATTGGCTCAGAAATATTAGGATTCGATGG

1040

CTCAGTGTGCCAAATCACAAAGATACAATCTTTTGTCCT

1080

TATAATGATGCTTATGTATTACCCATCCAGCAGAAGAGAT

1120

GCCTACAAGGTCAAACAAGGGATTGCGTGTTCACCCAGT

1160

TGCTGGCACTTTCCCTCGGAGATTTCTCACTACATATGGT

1200

ACTATAGTAGCTAATTGTAGAGATTAGTATGTTCTTGTC

1240

TCCGACCTCCTCAAATAATCTACCAACCTGATGAAAATCC

1280

AGTTACAATCATAGACAAAGACCTGTGTACAACATTGACT

1320

CTAGACTCCATCACTATAGAGATCCAGAAGTCCATAAATA

1360

GTACTTTTCGACGTGAAGTAGTTTTAGAATCTACTCAAGT

1400

CAGATCTTTGACTCCTCTTGATTTATCAACTGATTTAAAT

CAATACAATCAATTACTCAAGAGTGCTGAAGATCACATCC

1480

AAGCATCAACTGATTACTTAAACTCAATTAATCCTAGTAT

1520

AGTCAATAATAACGCAATAATAATATTGATTATACTCTGC

1560

ATCTTATTAATATTGACAGTTACAATCTGCATAATTTGGC

1600

TCAAGTATTTGACTAAGGAAGTTAAGAACGTGGCAAGAAA

1640

TCAAAGACTTAATAGAGATGCTGATCTTTTTTATAAGATC

1680

CCTAGTCAAATACCGGTGCCTAGATAATAACAGCCAAGAT

1720

TCATATTTTATAAACTTTATTTATCTAGATGCTCCAGGAA

1760

AAATCATCCACAAAGATGTACCAAATCTCATCTCATTGAA

1800

AGAAACTCAAAATCAACAGAATCACAACTATTCTACAACA

1840

ACACCACGACCATAACAATGTTCTCCAAGAAATGAGAGAC

1880

AAAGCCAGGAATCAGAAAAAATAGAAAGAACACAACAA

CAGACAGAGAAAAGAAGAAGAAGGGCAACATCGCCCTGG

1960

CAACACCCCAATCAACATCTCCAACCAAGACCGAATTG

2000

ACTGCAACCCGAACTCAACATCATAAAACGAGAAAGGG

2040

CCCCTCCACAATGGACCCCCTAGCCAGCTCGATCATCAA

2080

CAAAACAAAACGACACCCAATCAAACAATCTCCACATTTC

2120

AATTTTAAGAAAAAAA

MGVKGLSLIMIGLLISPITNLDITHLMNLGTVPTAIRSLV

41

YYTYTKPSYLTVDLIPNLKNLDQNCNYSSLNYYNKTALSL

81

IQPIADNINRLTKPITSSEIQSRFFGAVIGTIALGVATAA

121

QVTAAIGLAKAQENAKLILTLKKAATETNEAVRDLANSNK

161

IVVKMISAIQNQINTIILPAIDQINCQIKDLQVANILNLY

201

LTEITTVFHNQLTNPALESISISSQSSRTTYLPEVSSKLD

241

LNNISAASVMASGLIKGQIIAVDIPTMTLVLMVQIPSISP

281

LRQAKIIDLTSITIHTNSQEVQAVVPARFLEIGSEILGFD

321

GSVCQITKDTIFCPYNDAYVLPIQQKRCLQGQTRDCVFTP

361

VAGTFPRRFLTTYGTIVANCRDLVCSCLRPPQIIYQPDEN

401

PVTIIDKDLCTTLTLDSITIEIQKSINSTFRREVVLESTQ

441

VRSLTPLDLSTDLNQYNQLLKSAEDHIQASTDYLNSINPS

IVNNNAIIILIILCILLILTVTICIIWLKYLTKEVKNVAR

521

NQRLNRDADLFYKIPSQIPVPR

FIG. 3B

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2136 bases
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:

( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:1:

| | | | | |
|---|---|---|---|---|
| CCACCATCAA | GCACACAGCT | CCAAATCCTG | AGGTGATCAA | 4 0 |
| CACCCTTCGA | ATTCAATTCC | ATCACCAAAG | AATCCAACAT | 8 0 |
| GGGTGTCAAA | GGTTTATCTT | TAATTATGAT | TGGGTTATTA | 1 2 0 |
| ATCTCACCAA | TTACCAATCT | GGATATAACT | CATTTAATGA | 1 6 0 |
| ATCTAGGAAC | GGTACCGACT | GCAATTAGAT | CTCTAGTTTA | 2 0 0 |
| CTACACTTAT | ACCAAACCAT | CTTATCTCAC | TGTAGATTTG | 2 4 0 |
| ATTCCCAATT | TGAAGAATCT | GGACCAAAAT | TGCAATTACT | 2 8 0 |
| CAAGCTTAAA | CTACTACAAC | AAAACTGCAC | TAAGCCTAAT | 3 2 0 |
| TCAACCAATT | GCAGATAACA | TCAATCGCCT | TACAAAGCCC | 3 6 0 |
| ATCACAAGCT | CAGAAATTCA | AAGTCGTTTC | TTTGGGGCAG | 4 0 0 |
| TCATAGGTAC | AATTGCTCTT | GGTGTAGCCA | CCGCTGCACA | 4 4 0 |
| AGTTACAGCA | GCAATCGGTC | TAGCAAAAGC | TCAAGAAAAT | 4 8 0 |
| GCAAAACTTA | TACTAACTCT | CAAAAAAGCT | GCGACAGAAA | 5 2 0 |
| CAAATGAGGC | AGTTCGAGAT | CTTGCAAACT | CTAATAAAAT | 5 6 0 |
| TGTAGTAAAA | ATGATATCAG | CAATTCAAAA | TCAAATAAAC | 6 0 0 |
| ACTATTATTC | TTCCTGCTAT | AGATCAGATT | AATTGTCAAA | 6 4 0 |
| TTAAAGACCT | ACAAGTTGCC | AATATTTTAA | ATTTGTACCT | 6 8 0 |
| AACAGAGATA | ACGACTGTTT | TCCACAACCA | ATTGACCAAT | 7 2 0 |
| CCTGCATTAG | AGTCAATTAG | CATCAGCTCT | CAAAGCTCTA | 7 6 0 |
| GGACTACCTA | CCTACCAGAA | GTGTCATCTA | AATTAGATTT | 8 0 0 |
| AAACAACATC | TCGGCAGCTT | CAGTGATGGC | ATCCGGCTTA | 8 4 0 |
| ATTAAAGGAC | AGATAATTGC | AGTTGATATA | CCGACTATGA | 8 8 0 |
| CACTAGTATT | GATGGTCCAA | ATACCGAGTA | TATCCCCTTT | 9 2 0 |
| AAGACAAGCA | AAGATAATAG | ATCTAACTTC | TATAACAATT | 9 6 0 |

| | | | | |
|---|---|---|---|---|
| CACACAAATA | GCCAAGAAGT | ACAGGCTGTA | GTACCGGCTA | 1000 |
| GGTTTCTCGA | GATTGGCTCA | GAAATATTAG | GATTCGATGG | 1040 |
| CTCAGTGTGC | CAAATCACAA | AAGATACAAT | CTTTTGTCCT | 1080 |
| TATAATGATG | CTTATGTATT | ACCCATCCAG | CAGAAGAGAT | 1120 |
| GCCTACAAGG | TCAAACAAGG | GATTGCGTGT | TCACCCCAGT | 1160 |
| TGCTGGCACT | TTCCCTCGGA | GATTTCTCAC | TACATATGGT | 1200 |
| ACTATAGTAG | CTAATTGTAG | AGATTAGTA | TGTTCTTGTC | 1240 |
| TCCGACCTCC | TCAAATAATC | TACCAACCTG | ATGAAAATCC | 1280 |
| AGTTACAATC | ATAGACAAAG | ACCTGTGTAC | AACATTGACT | 1320 |
| CTAGACTCCA | TCACTATAGA | GATCCAGAAG | TCCATAAATA | 1360 |
| GTACTTTTCG | ACGTGAAGTA | GTTTTAGAAT | CTACTCAAGT | 1400 |
| CAGATCTTTG | ACTCCTCTTG | ATTTATCAAC | TGATTTAAAT | 1440 |
| CAATACAATC | AATTACTCAA | GAGTGCTGAA | GATCACATCC | 1480 |
| AAGCATCAAC | TGATTACTTA | AACTCAATTA | ATCCTAGTAT | 1520 |
| AGTCAATAAT | AACGCAATAA | TAATATTGAT | TATACTCTGC | 1560 |
| ATCTTATTAA | TATTGACAGT | TACAATCTGC | ATAATTTGGC | 1600 |
| TCAAGTATTT | GACTAAGGAA | GTTAAGAACG | TGGCAAGAAA | 1640 |
| TCAAAGACTT | AATAGAGATG | CTGATCTTTT | TTATAAGATC | 1680 |
| CCTAGTCAAA | TACCGGTGCC | TAGATAATAA | CAGCCAAGAT | 1720 |
| TCATATTTTA | TAAACTTTAT | TTATCTAGAT | GCTCCAGGAA | 1760 |
| AAATCATCCA | CAAAGATGTA | CCAAATCTCA | TCTCATTGAA | 1800 |
| AGAAACTCAA | AATCAACAGA | ATCACAACTA | TTCTACAACA | 1840 |
| ACACCACGAC | CATAACAATG | TTCTCCAAGA | AATGAGAGAC | 1880 |
| AAAGCCAGGA | ATCAGAAAAA | AATAGAAAAG | AACACAACAA | 1920 |
| CAGACAGAGA | AAAAGAAGAA | GAAGGGCAAC | ATCGCCCTGG | 1960 |
| CAACACCCCC | AATCAACATC | TCCCAACCAA | GACCGAATTG | 2000 |
| ACTGCACAAC | CCGAACTCAA | CATCATAAAA | CGAGAAGGG | 2040 |
| CCCCTCCACA | ATGGACCCCC | CTAGCCAGCT | CGATCATCAA | 2080 |
| CAAAACAAAA | CGACACCCAA | TCAAACAATC | TCCACATTTC | 2120 |
| AATTTTAAGA | AAAAAA | | | 2136 |

( 2 ) INFORMATION FOR SEQ ID NO:2:

( i ) SEQUENCE CHARACTERISTICS:
        ( A ) LENGTH: 542 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:

(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:2:

```
Met Gly Val Lys Gly Leu Ser Leu Ile Met Ile Gly Leu Leu Ile Ser
 1               5                  10                      15

Pro Ile Thr Asn Leu Asp Ile Thr His Leu Met Asn Leu Gly Thr Val
            20                  25                  30

Pro Thr Ala Ile Arg Ser Leu Val Tyr Tyr Thr Tyr Thr Lys Pro Ser
            35                  40                  45

Tyr Leu Thr Val Asp Leu Ile Pro Asn Leu Lys Asn Leu Asp Gln Asn
     50                  55                  60

Cys Asn Tyr Ser Ser Leu Asn Tyr Tyr Asn Lys Thr Ala Leu Ser Leu
 65                  70                  75                      80

Ile Gln Pro Ile Ala Asp Asn Ile Asn Arg Leu Thr Lys Pro Ile Thr
                 85                  90                  95

Ser Ser Glu Ile Gln Ser Arg Phe Phe Gly Ala Val Ile Gly Thr Ile
            100                 105                 110

Ala Leu Gly Val Ala Thr Ala Ala Gln Val Thr Ala Ala Ile Gly Leu
            115                 120                 125

Ala Lys Ala Gln Glu Asn Ala Lys Leu Ile Leu Thr Leu Lys Lys Ala
            130                 135                 140

Ala Thr Glu Thr Asn Glu Ala Val Arg Asp Leu Ala Asn Ser Asn Lys
145                 150                 155                 160

Ile Val Val Lys Met Ile Ser Ala Ile Gln Asn Gln Ile Asn Thr Ile
                165                 170                 175

Ile Leu Pro Ala Ile Asp Gln Ile Asn Cys Gln Ile Lys Asp Leu Gln
            180                 185                 190

Val Ala Asn Ile Leu Asn Leu Tyr Leu Thr Glu Ile Thr Thr Val Phe
            195                 200                 205

His Asn Gln Leu Thr Asn Pro Ala Leu Glu Ser Ile Ser Ile Ser Ser
     210                 215                 220
```

```
Gln  Ser  Ser  Arg  Thr  Thr  Tyr  Leu  Pro  Glu  Val  Ser  Ser  Lys  Leu  Asp
225                 230                 235                      240

Leu  Asn  Asn  Ile  Ser  Ala  Ala  Ser  Val  Met  Ala  Ser  Gly  Leu  Ile  Lys
                245                      250                      255

Gly  Gln  Ile  Ile  Ala  Val  Asp  Ile  Pro  Thr  Met  Thr  Leu  Val  Leu  Met
           260                      265                           270

Val  Gln  Ile  Pro  Ser  Ile  Ser  Pro  Leu  Arg  Gln  Ala  Lys  Ile  Ile  Asp
           275                      280                      285

Leu  Thr  Ser  Ile  Thr  Ile  His  Thr  Asn  Ser  Gln  Glu  Val  Gln  Ala  Val
     290                      295                      300

Val  Pro  Ala  Arg  Phe  Leu  Glu  Ile  Gly  Ser  Glu  Ile  Leu  Gly  Phe  Asp
305                      310                      315                      320

Gly  Ser  Val  Cys  Gln  Ile  Thr  Lys  Asp  Thr  Ile  Phe  Cys  Pro  Tyr  Asn
                325                      330                      335

Asp  Ala  Tyr  Val  Leu  Pro  Ile  Gln  Gln  Lys  Arg  Cys  Leu  Gln  Gly  Gln
                340                      345                 350

Thr  Arg  Asp  Cys  Val  Phe  Thr  Pro  Val  Ala  Gly  Thr  Phe  Pro  Arg  Arg
          355                      360                      365

Phe  Leu  Thr  Thr  Tyr  Gly  Thr  Ile  Val  Ala  Asn  Cys  Arg  Asp  Leu  Val
     370                      375                 380

Cys  Ser  Cys  Leu  Arg  Pro  Pro  Gln  Ile  Ile  Tyr  Gln  Pro  Asp  Glu  Asn
385                 390                      395                      400

Pro  Val  Thr  Ile  Ile  Asp  Lys  Asp  Leu  Cys  Thr  Thr  Leu  Thr  Leu  Asp
               405                      410                      415

Ser  Ile  Thr  Ile  Glu  Ile  Gln  Lys  Ser  Ile  Asn  Ser  Thr  Phe  Arg  Arg
               420                      425                 430

Glu  Val  Val  Leu  Glu  Ser  Thr  Gln  Val  Arg  Ser  Leu  Thr  Pro  Leu  Asp
          435                      440                 445

Leu  Ser  Thr  Asp  Leu  Asn  Gln  Tyr  Asn  Gln  Leu  Leu  Lys  Ser  Ala  Glu
     450                      455                 460

Asp  His  Ile  Gln  Ala  Ser  Thr  Asp  Tyr  Leu  Asn  Ser  Ile  Asn  Pro  Ser
465                      470                 475                      480

Ile  Val  Asn  Asn  Asn  Ala  Ile  Ile  Ile  Leu  Ile  Ile  Leu  Cys  Ile  Leu
               485                      490                      495

Leu  Ile  Leu  Thr  Val  Thr  Ile  Cys  Ile  Ile  Trp  Leu  Lys  Tyr  Leu  Thr
               500                 505                      510

Lys  Glu  Val  Lys  Asn  Val  Ala  Arg  Asn  Gln  Arg  Leu  Asn  Arg  Asp  Ala
          515                      520                 525

Asp  Leu  Phe  Tyr  Lys  Ile  Pro  Ser  Gln  Ile  Pro  Val  Pro  Arg
     530                 535                 540
```

( 2 ) INFORMATION FOR SEQ ID NO:3:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:

```
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

ATGAATCTAG GAACGGTACC GA                                              2 2
```

HUMAN PARAINFLUENZA VIRUS TYPE 4A FUSION PROTEIN AND GENE CODING FOR THE SAME

This application is a continuation of Ser. No. 07/915,826, filed as PCT/JP91/01402, Oct. 15, 1991 published as WO92/09693, Jun. 11, 1992, now abandoned.

BACKGROUND OF THE INVENTION

1. Field of the Invention

The present invention relates to a human parainfluenza virus type 4A (PIV-4A) fusion protein (F protein), a gene coding for the same and its application.

2. Background Art

In order to enhance a therapeutic effect of a virus infectious disease, it is necessary to identify the infection virus and to conduct a proper treatment based on the results of the identification.

In general, virus has hitherto been identified based on serological properties. Typical examples of such a method known in the art include enzyme-linked immunosorbent assay (ELISA), neutralization reaction method, complement fixation reaction, hemagglutination inhibition reaction, fluorescent antibody technique and agar precipitation reaction. In all the above-described methods, the presence or absence of a virus is determined through the determination of an antibody to the virus in a sample. Therefore, in order to determine the presence or absence of a virus with a high accuracy, the determination of the antibody should have been generally conducted about one week after the infection at a stage in which the virus antibody titer begins to increase. In some cases, redetermination for identification should have been conducted several weeks after the first determination. Thus, the prior art methods had a problem that it is difficult to conduct the diagnosis before onset of a viral disease or at an early stage of the onset of a viral disease.

ELISA is generally used for the determination of PIV-4A. In this method, an antibody to PIV-4A is determined. For example, the determination is conducted by adding a sample to a plate having PIV-4A immobilized thereon, allowing a reaction to proceed, washing the sample, further adding an anti-PIV-4A antibody, allowing a reaction to proceed and developing a color. In this method as well, it is difficult to conduct the diagnosis before onset of a viral disease or at an early stage of the onset of a viral disease, so that the initiation of the treatment is delayed, which unfavorably makes it difficult to enhance the therapeutic effect.

SUMMARY OF THE INVENTION

Accordingly, an object of the present invention is to provide a PIV-4A•F protein which enables a PIV-4A infective disease to be diagnosed at an early stage and treated, and a gene coding for the same.

Another object of the present invention is to provide a diagnostic composition and a diagnostic method for a PIV-4A infective disease.

The DNA sequence according to the present invention comprises a base sequence having the whole or a part of a base sequence shown in FIGS. 2A to 2E (SEQ ID NO. 1), or comprising a base sequence hybridizable with a base sequence shown in FIGS. 2A to 2E.

The PIV-4A•F protein has an amino acid sequence shown in FIGS. 3A and 3B (SEQ ID NO. 2).

Further, the DNA sequence according to the present invention comprises a base-sequence coding for an amino acid sequence shown in FIGS. 3A and 3B, or a base sequence hybridizable with a base sequence coding for an amino acid sequence shown in FIGS. 3A and 3B.

Further, the diagnostic composition for detecting the presence or absence of RNA for PIV-4A according to the present invention comprises the above-described DNA sequence according to the present invention and a carrier therefor.

Further, the diagnostic method of detecting the presence or absence of RNA for PIV-4A according to the present invention comprises reacting the above-described DNA sequence according to the present invention with a sample and determining the occurrence of hybridization.

BRIEF DESCRIPTION OF THE DRAWINGS

FIGS. 2A to 2E are each a diagram showing a base sequence for a cDNA region complementary to a PIV-4A•F protein gene contained in clone p4AF; and FIGS. 3A and 3B is a diagram showing an amino acid sequence for a PIV-4A•F protein.

DETAILED DESCRIPTION OF THE INVENTION

DNA sequence

Figure 1:
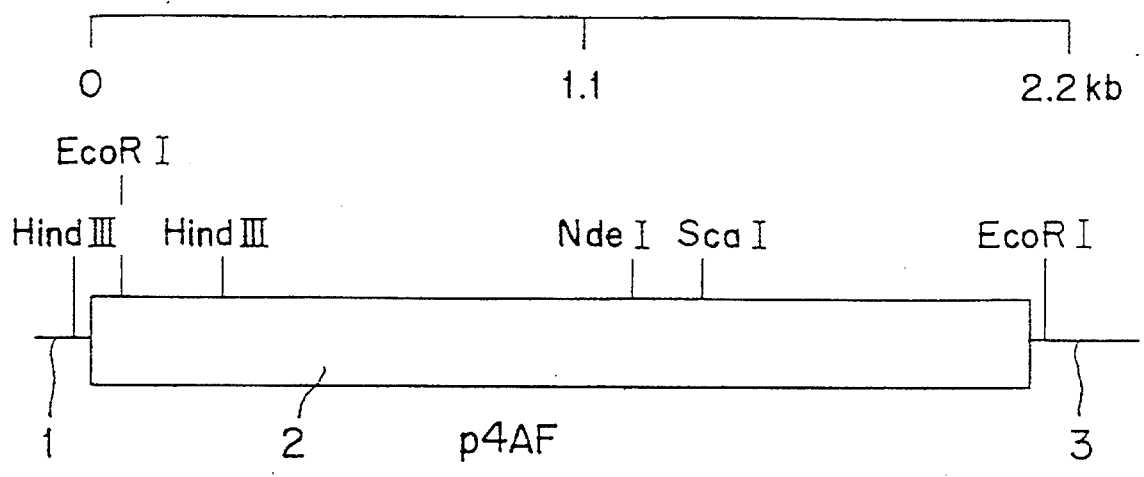
FIG. 1 is a restriction enzyme map for a cDNA region complementary to a PIV-4A•F protein gene contained in clone p4AF.

The base sequence shown in FIG. 2 is for a sequence complementary to a gene derived from PIV-4A in p4AF which is a clone obtained from a mRNA-derived library obtained from cells infected with PIV-4A, that is, cDNA. An open reading frame beginning with an ATG codon at nucleotides 78–80 and ending with a TAA termination codon at nucleotides 1704–1706 exists in the base sequence shown in FIG. 2. The sequence 78–1706 codes for an amino acid sequence shown in FIG. 3. The sequence shown in FIG. 3 is a membrane protein of a virus called a "PIV- 4A•F protein".

The F protein protrudes in the form of a spike on a virion membrane. It exhibits activities in hemolysis, membrane fusion, cell fusion, etc. and plays an important role in the mechanism through which cells are infected with a virus. Further, since the F protein has an influence as an antigen on the production of a phylactic antibody on an individual level, it has been viewed to be very important.

According to one aspect of the present invention, there is provided a DNA sequence comprising a base sequence having the whole or a part of a base sequence shown in FIG. 2.

According to another aspect of the present invention, there is provided a PIV-4A•F protein having an amino acid sequence shown in FIG. 3. A typical sequence of DNA coding for this protein has the base sequence 78–1706 shown in FIG. 2. When an amino acid sequence for the protein is further provided, the base sequence coding for the amino acid sequence is easily determined with reference to the so-called "genetic code table", so that various base sequences coding for the amino acid sequence shown in FIG. 3 can be properly selected. Therefore, the term "the base sequence coding for the amino acid sequence shown in FIG. 3" in this disclosure is intended to mean the base sequence having the sequence 78–1706 shown in FIG. 2 and a base sequence coding for the peptide shown in FIG. 3 except that a codon in the degeneracy relation is used.

Further, according to a further aspect of the present invention, there is provided a base sequence hybridizable with a base sequence shown in FIG. 2 or a base sequence coding for an amino acid sequence shown in FIG. 3. Examples of the base sequence of this type include a base sequence completely complementary to a base sequence shown in FIG. 2; a base sequence coding for an amino acid sequence shown in FIG. 3; and a base sequence containing a portion of the base sequences; and further a base sequence having a complementation sufficient to bring a hybridization reaction with a base sequence shown in FIG. 2 or a base sequence coding for an amino acid sequence shown in FIG. 3 although some bases are substituted or deleted.

Acquisition of DNA Sequence

Since the DNA according to the present invention has a fixed base sequence, one means for acquiring the DNA is to produce the DNA according to a technique for synthesizing a nucleic acid. For example, a synthetic nucleotide can be obtained according to a phosphoamidite method (Nature, vol. 310, 105, 1984) based on the base sequence shown in FIG. 2.

Further, the DNA according to the present invention can be obtained from a genome library derived from PIV-4A according to a method commonly used in the field of genetic engineering. For example, the DNA according to the present invention can be obtained by inserting cDNA prepared from mRNA obtained from cells infected with PIV- 4A into a suitable vector (for example, a plasmid vector) of a suitable host (for example, E. coli), subjecting the insert to cloning in the host, isolating a clone coding for a PIV-4A•F protein gene by a method such as (i) a method wherein screening is conducted through the use of nucleocapsid RNA as a probe, (ii) a method wherein screening is conducted through the use of an oligonucleotide synthesized based on the base sequence shown in FIG. 2 as a probe, or (iii) a method wherein screening is conducted through the use of an antibody to PIV-4A, and separating an insert DNA from the vector of the isolated clone.

Use of DNA Sequence

Since the DNA according to the present invention is complementary to a gene for a PIV-4A•F protein, a DNA fragment having the whole or a part of the base sequence shown in FIG. 2 is hybridizable with a gene derived from PIV-4A, for example, mRNA. Accordingly, the present invention provides a diagnostic method and a diagnostic composition for detecting the presence or absence of RNA of PIV-4A in a sample, especially mRNA of a PIV-4A•F protein. The method and diagnostic composition according to the present invention enables a PIV-4A infective disease to be diagnosed at an early stage as compared with the prior art method wherein use is made of an immunological technique.

When the base sequence shown in FIG. 2 is utilized in the diagnostic method and diagnostic composition according to the present invention, although it is possible to use the whole of the base sequence, the base sequence is preferably used in the form of a DNA fragment having a suitable length. For example, the DNA having a base sequence shown in FIG. 2 is preferably used in the form of a fragment having ten-odd or more bp, preferably 20 bp or more, prepared through the use of a suitable restriction enzyme.

The diagnostic composition of the present invention comprises the above-described DNA fragment and a suitable carrier therefor. According to a preferred embodiment of the present invention, the carrier may be a liquid capable of dissolving the DNA fragment. Alternatively, it may be a polymer, cellulose, a glass bead, a medicine or other compound capable of holding the DNA fragment through a physical or chemical bond. Further, it is possible to use a DNA vector as the carrier into which the DNA fragment is integrated.

The diagnostic method according to the present invention comprises reacting the above-described DNA fragment with RNA of PIV-4A extracted from a sample (for example, a pharynx liquid) and determining the occurrence of hybridization. The determination of the occurrence of hybridization is conducted, for example, by a Northern hybridization method which comprises labeling a DNA fragment with a radioactive isotope or the like, reacting the labeled DNA fragment with RNA (which is preferably immobilized on a suitable carrier, for example, a nylon membrane) of PIV-4A extracted from a sample, and detecting the presence or absence of a signal from the label.

A DNA containing a base sequence hybridizable with a base sequence shown in FIG. 2 or a base sequence coding for an amino acid sequence shown in FIG. 3 may be used as the DNA fragment used in the diagnostic method and diagnostic composition according to the present invention.

Expression of DNA Sequence and Expression Product Thereof

As described above, the base sequence shown in FIG. 2 contains an open reading frame of nucleotides 78–1706. This open reading frame codes for an amino acid sequence shown in FIG. 3. Therefore, a polypeptide having an amino acid sequence shown in FIG. 3 can be prepared by inserting the base sequence into a vector so that the base sequence is expressable, thereby obtaining an expression vector, and expressing the base sequence in a suitable host. The base sequence shown in FIG. 2 is also considered to contain a control region for expression of an open reading frame. Therefore, in some cases, it is preferred that the base sequence to be inserted into the expression vector have the whole of the sequence shown in FIG. 2, or the whole or a part of the base sequences upstream or downstream of the open reading frame.

Accordingly, the present invention provides an expression vector for a PIV-4A•F protein. The expression vector according to the present invention contains a DNA sequence including a base sequence comprising the whole or a part of a base sequence shown in FIG. 2 in such a state that the DNA sequence is replicable in host cells and a gene coding for a PIV-4A•F protein is expressable. The host-vector system is not particularly limited and may be any of procaryote cells and eucaryote cells, and examples thereof include a system wherein use is made of microorganisms such as E. coli and Bacillus subtilis and a system wherein use is made of cells of yeast, insects, mammals, etc. Further, it is possible to utilize an in vitro synthetic system wherein use is made of a rabbit erythrocyte lysate.

The thus obtained polypeptide as an expression product can be used for applications such as antigen for preparation of antibodies and a starting material for vaccines. These antibodies and vaccines are expected to be used for diagnosis and treatment of PIV-4A infective diseases.

EXAMPLES

Example 1
Preparation of RNA

Primary monkey kidney cells were grown in an Eagle's essential medium containing 5% fetal calf serum, and the medium was replaced with a freshly prepared Eagle's essential medium containing actinomycin D (2 μg/ml). Then, PIV-4A (Toshiba strain) was inoculated into the medium and incubated in the medium for 24 hr. Cultured cells infected with the virus were peeled off with a mixed solution comprising trypsin and EDTA and subjected to centrifugation at 8000 rpm for 10 min to collect the cells. A guanidine isothiocyanate solution (6M guanidine isothiocyanate, 5 mM sodium citrate, 0.1M 2-mercaptoethanol, and 0.5% sodium uraloylsarcosinate) was added to the cells, and lysis was rapidly conducted in a homogenizer. The lysate was passed five times through an injection cylinder equipped with a 21G injection needle to shear the chromosome DNA. The resultant cytolysate was again subjected to centrifugation at 8000 rpm, and 9 ml of the supernatant was overlaid in a separate centrifuging tube containing 3 ml of a 5.7M aqueous cesium chloride solution. Ultracentrifugation was conducted at 18° C. in a Beckman rotor (Beckman SW40Ti rotor) at 37000 rpm for 18 hr. After the centrifugation, RNA pellets were collected.

mRNA containing a poly A chain (hereinafter referred to as "poly(A+)RNA") was isolated from the resultant RNA and purified through the use of oligo dT cellulose type 7 (manufactured by Pharmacia).

Example 2
Preparation of cDNA Library

A cDNA library was synthesized according to a Okayama-Berg method. Specifically, 5 μl of distilled water was added to 4 μg of poly(A+)RNA, and the mixture was heated at 65° C. for 10 min and then rapidly cooled. Thereafter, 10 μl of oligo dT primed vector (prepared by adding oligo dT to KpnI site of pUC118 vector (0.8 to 1.2 μg/μl)), 3 μl of a synthetic reaction solution (500 nM Tris-HCl buffer (pH 8.3), 300 mM potassium chloride, 80 mM magnesium chloride, 3 mM dithiothreitol), and 1 μl of each of 20 mM dATP, 20 mM dCTP, 20 mM dGTP and 20 mM dTTP were added thereto. Further, 20 units of RNasin and 40 units of reverse transcriptase were added, and distilled water was then added to a total volume of 30 μl. The mixture was allowed to react at 42° C. for 30 min to synthesize a first chain cDNA. After the completion of synthesis of the first chain cDNA, 10 to 30 dG bases were added through the use of terminal deoxynucleotidyl transferase in the presence of dGTP. Then, the product was digested with restriction enzyme Hind III, annealed with a linker having a dC base chain and subjected to cyclization with E. coli ligase. Finally, a second chain was synthesized through the use of DNA polymerase in the presence of RNaseH to prepare a complete plasmid DNA.

Then, to 100 to 200 μl of competent cells (DHI) obtained by a calcium chloride treatment were added 10 μl of a mixed solution comprising 0.4M magnesium chloride and 0.1M calcium chloride and 0.02 μg of the above-described plasmid DNA. The mixture was allowed to stand at 0° C. for 40 min and then at 42° C. for 90 sec, and 1.5 ml of a medium (a solution prepared by dissolving 10 g of bactotryptone, 5 g of yeast extract and 5 g of sodium chloride in 1000 ml of distilled water) was added thereto. The mixture was allowed to stand at 37° C. for 40 min to prepare transformed cells.

Thus, independent 1500 clones were obtained in the presence of ampicillin through the introduction of 0.02 μg of plasmid DNA in 200 μl of competent cells (DHl).

Example 3
Preparation of Nucleocapsid RNA

To primary monkey kidney cells infected with PIV-4A was added a solution (0.15M sodium chloride, 0.05M Tris-HCl buffer) containing 0.6% Nonidet P-40 and 10 mM vanadyl ribonucleotide composite, and solubilization was conducted in ice by pipetting for 1 hr, followed by centrifugation at 8000 rpm for 10 min. In a centrifuging tube wherein 1 ml of a 40% aqueous cesium chloride solution, 2.5 ml of a 30% aqueous cesium chloride solution and 1 ml of a 25% aqueous cesium chloride solution were overlaid in that order, 9 ml of the supernatant obtained by the above centrifugation was further overlaid thereon, and equilibrium density gradient centrifugation was conducted at 16° C. by means of a Beckman rotor SW40Ti at 37000 rpm for 18 hr. After the centrifugation, a nucleocapsid band of virus formed in the 30% aqueous cesium chloride solution layer was collected. Then, 0.1% SDS and proteinase K (2.5 mg/ml) were added thereto, and proteolysis was conducted at 56° C. for 15 min. The reaction mixture was treated with a mixed solution comprising phenol and mixture of phenol and chloroform to give nucleocapside RNA. To the resultant nucleocapside RNA was added 50 mM Tris-HCl buffer (pH 9.7). The mixture was heated at 95° C. for 10 min and then gradually cooled to room temperature. To 20 μl of the RNA solution were added 10 μl of a buffer (250 mM Tris-HCl, 50 mM magnesium chloride, 25 mM DTT, 7.5 mM spermine, 500 mM potassium chloride), 3 μl of $^{32}$PATP (100 μCi/600 pM) and 2 units of T4-DNA kinase, and distilled water was added thereto to a total volume of 50 μl. The mixture was allowed to react at 37° C. for 1 hr to give a nucleocapsid RNA probe.

Example 4
Colony Hybridization 100 to 200 μl of the transformed cells obtained in Example 2 was sowed in a 15-cm agar plate (prepared by adding 10 g of bactotryptone, 5 g of yeast extract, 5 g of sodium chloride and 15 g of agar and adding distilled water thereto to a total volume of 1000 ml) containing ampicillin (120 μg/ml) and incubated at 37° C. for 12 hr. The resultant colony was transferred to a nitrocellulose membrane and incubated at 37° C. for 6 hr. Then, the membrane was treated with a mixed solution containing 0.5 N sodium hydroxide and 1.5M sodium chloride for 10 min, allowed to stand in a 0.5M Tris-HCl buffer (pH 8.0) containing 1.5M sodium chloride for 10 min, and rinsed in a mixed solution comprising 0.3M sodium chloride and 0.03M sodium citrate for 5 min. After rinsing, the membrane was air-dried and baked at 80° C. with suction for one hour to immobilize DNA on the membrane.

To five sheets of membranes thus obtained was added a prehybridization solution containing 1 ml of modified salmon RNA (1 mg/ml), 7.5 ml of a SSPE solution (3.6M sodium chloride, 200 mM sodium primary phosphate, 20 mM EDTA), 1.25 ml of a Denhardt's solution (2% BSA, 2% Ficoll, 2% polyvinylpyrrolidone) and 1.25 ml of 10% SDS, and the mixture was allowed to react at 42° C. for 12 hr. Then, the nucleocapsid RNA probe obtained in Example 3 was added so as to have a concentration of 5,000,000 Ci/ml to the freshly prepared prehybridization solution of the type described above, and the mixture was allowed to react at 42° C. for 18 hr.

After the completion of the reaction, the membranes were washed twice in a SSPE solution (diluted 20 times) containing 0.1% SDS at 42° C. for 5 min, and washed twice in a SSPE solution (diluted 200 times) containing 0.1% SDS at 42° C. for 5 min. After the completion of washing, the membranes were air-dried, and several positive clones were obtained by autoradiography at −80° C. for 12 hr through the use of an X-ray film (RX5 manufactured by Kodak).

Example 5
Northern Hybridization Method

The above positive clones were subjected to northern hybridization. Specifically, poly(A+)RNA derived from cells infected with PIV-4A, poly(A+)RNA derived from cells noninfected with the virus obtained by the above-described method (1) and an rRNA marker were each electrophoresed on a 1.5% agarose gel, transferred to a nylon membrane (Hybond N manufactured by Amersham Int., Ple.), air-dried and irradiated with UV to covalently bond RNA to the nylon membrane.

Then, hybridization was conducted through the use of each positive clone as a probe obtained in Example 4. Specifically, the nylon membrane was allowed to react in the above-described prehybridization solution at 42° C. for 12 hr, and a probe labelled with $^{32}P$ prepared from each positive clone was added to the prehybridization solution so as to have a concentration of 1,000,000 Ci/ml. A reaction then proceeded at 42° C. for 18 hr. After the completion of the reaction, washing was conducted in the same manner as that of Example 4, and autoradiography was then conducted through the use of an X-ray film. As a result, one clone hybridized at a position of about 2100 base was obtained. This clone was designated as "p4AF". A probe for each positive clone was obtained by digesting each clone with Hind III and EcoR I, separating insert DNA by electrophoresis through the use of an agarose having a low melting point, conducting extraction and subjecting the extract to random prime labelling through the use of $^{32}PdCTP$.

Example 6

Construction of Restriction Enzyme Map and Determination of Base Sequence of DNA Complementary to PIV-4A•F Protein Gene Clone p4AF obtained in Example 5 was cleaved with various restriction enzymes to construct a restriction enzyme map.

FIG. 1 is a restriction enzyme map constructed by cleaving clone p4AF with respective restriction enzymes of Hind III, Nde I, Sca I and EcoR I, inserting the resultant fragments into multicloning sites of plasmid pUC118, and conducting sequencing through the use of SEQUENASE TM kit (manufactured by Toyobo Co., Ltd.) and preparing a deletion mutant from part of it through the use of a kilosequence deletion kit (manufactured by Takara Shuzo Co., Ltd.), and conducting sequencing to determine a base sequence. In the drawing, numerals 1 and 3 designate vector DNA, and numeral 2 insert DNA which is the DNA fragment according to the present invention. The resultant base sequence is as shown in FIG. 2.

Example 7

Identification of PIV-4A (1) When use is made of the whole of the insert DNA

The p4AF clone obtained in Example 5 was cleaved with Pst I and Sac I, and a band migrated at about 2100 bp by electrophoresis on an agarose gel having a low melting point was cut, extracted and precipitated from ethanol to collect insert DNA. To 1 μl of the resultant DNA (10 pmoles/μl) were added 2 μl of a buffer (0.5M Tris-HCl (pH 7.6, 0.1M MgCl$_2$, 50 mM dithiothreitol, 1 mM spermidine hydrochloride, 1 mM EDTA), 11.4 μl of distilled water, 5 μl of ($\gamma^{32}P$)ATP (2 nmoles/μl) and 8 units of bacteriophage T4 polynucleotide kinase, and the mixture was allowed to react at 37° C. for 45 min. Then, the reaction mixture was purified by Bio-gel P60 (manufactured by Nippon Bio-Rad Laboratories Co., Ltd.), and the resultant purification product was used as a probe.

The RNA derived from cells infected with PIV-4A and RNA derived from cells mock-infected with the virus obtained in the method described in Example 1 were each plotted in an amount of 0.35 μg on a nylon membrane, air-dried, irradiated with UV and allowed to react in the prehybridization solution described in Example 4 at 42° C. for 12 hr. Then, the above probe which had been allowed to stand in a boiling water bath for 2 min and then rapidly cooled was added thereto so as to have a concentration of 1,000,000 Ci/ml, and the mixture was allowed to react at 42° C. for 18 hr. After the completion of the reaction, the membrane was washed twice in a SSPE solution (diluted 20 times) containing 0.1% SDS at 42° C. for 5 min, and washed twice in a SSPE solution (diluted 200 times) containing 0.1% SDS at 42° C. for 5 min. After the completion of washing, the membranes were air-dried, and autoradiography was conducted at −80° C. for 12 hr through the use of an X-ray film.

As a result, a positive signal generated by the probe hybridized with the PIV-4A virus RNA in the sample was observed on a portion where the RNA derived from cells infected with PIV-4A has been plotted. That is, infection with PIV-4A was confirmed. On the other hand, no reaction was observed on a portion where the RNA derived from cells mock-infected with the virus has been plotted.

(2) When use is made of partial fragment of insert DNA

The p4AF clone obtained in Example 5 was cleaved with Bgl II, and a band migrated at about 350–450 bp by electrophoresis on an agarose gel having a low melting point was cut, extracted and precipitated from ethanol to collect a DNA fragment.

The DNA fragment thus obtained was subjected to random prime labelling to form a probe. Specifically, 10 μl of distilled water was added to 0.1 μg of the DNA fragment, and the mixture was allowed to stand in a boiling water for 2 min and rapidly cooled. To the cooled mixture were added 1 μl (10 mg/ml) of bovine serum albumin, 11.4 μl of a random solution [0.44M HEPES (pH 6.6), 110 mM Tris-HCl (pH 8), 11 mM MgCl$_2$, 22 mM 2-mercaptoethanol, 44 μM dATP, 44 μM dGTP, 44 μM dTTP, 0.12 mM Tris-HCl (pH 7.5), 0.12 mM EDTA, 11 units/ml oligonucleotide pd(N)$_6$ (manufactured by Pharmacia)], 5 μl (100 μCi/600 pM) of ($\alpha^{32}P$) dCTP and 2.5 units of Klenow, and the mixture was allowed to react at room temperature for 6 hr. The resultant reaction mixture was purified by Bio-gel P60 and used as a probe.

The RNA derived from cells infected with PIV-4A and RNA derived from cells mock-infected with the virus obtained in the method described in Example 1 were each plotted in an amount of 0.35 μg on a nylon membrane, air-dried, irradiated with UV and allowed to react in the prehybridization solution described in Example 4 at 42° C. for 12 hr. Then, the above probe which had been allowed to stand in a boiling water bath for 2 min and then rapidly cooled was added thereto so as to have a concentration of 1,000,000 Ci/ml, and the mixture was allowed to react at 42° C. for 18 hr. After the completion of the reaction, the membrane was washed twice in a SSPE solution (diluted 20 times) containing 0.1% SDS at 42° C. for 5 min, and washed twice in a SSPE solution (diluted 200 times) containing 0.1% SDS at 42° C. for 5 min. After the completion of washing, the membranes were air-dried, and autoradiography was conducted at −80° C. for 12 hr through the use of an X-ray film.

As a result, a positive signal generated by the probe hybridized with the PIV-4A virus RNA in the sample was observed on a portion where the RNA derived from cells infected with PIV-4A has been plotted. That is, infection with PIV-4A was confirmed. On the other hand, no reaction was observed on a portion where the RNA derived from cells mock-infected with the virus has been plotted.

(3) When use is made of synthetic oligonucleotide

An oligonucleotide having ten-odd or more bp was synthesized according to the base sequence shown in FIG. 2 and used as a probe.

Specifically, an oligonucleotide (5'-ATGAATCTAG-GAACGGTACCGA-3') (SEQ ID NO. 3) synthesized through the use of a DNA synthesizer (DNA synthesizer Model 381A manufactured by Applied Biosystems Inc.) was purified through the use of an oligonucleotide purification cartridge (manufactured by Applied Biosystems Inc.). To 1 μl (10 pmoles/μl) of the resultant synthesized oligonucleotide were added 2 μl of a buffer of the above (1), 11.4 μl of distilled water, 5 μl (2 nmoles/μl) of ($\gamma^{32}$P) ATP and 8 units of bacteriophage T4 polynucleotide kinase, and the mixture was allowed to react at 37° C. for 45 min. Then, the reaction mixture was purified by Bio-gel P60, and the resultant purification product was used as a probe.

The RNA derived from cells infected with PIV-4A and RNA derived from cells noninfected with the virus obtained in the method described in Example 1 were each plotted in an amount of 0.35 μg on a nylon membrane, air-dried, irradiated with UV and allowed to react in the prehybridization solution described in Example 4 at 42° C. for 12 hr. Then, the above probe was added thereto so as to have a concentration of 1,000,000 Ci/ml, and the mixture was allowed to react at 42° C. for 18 hr. After the completion of the reaction, the membrane was washed twice in a SSPE solution (diluted 20 times) containing 0.1% SDS at 42° C. for 5 min, and washed twice in a SSPE solution (diluted 200 times) containing 0.1% SDS 42° C. for 15 min. After the completion of washing, the membranes were air-dried, and autoradiography was conducted at −80° C. for 12 hr through the use of an X-ray film.

As a result, a positive signal generated by the probe hybridized with the PIV-4A virus RNA in the sample was observed on a portion where the RNA derived from cells infected with PIV-4A had been plotted. That is, infection with PIV-4A was confirmed. On the other hand, no reaction was observed on a portion where the RNA derived from cells mock-infected with the virus has been plotted.

Example 8

Expression of p4AF Clone Coding for Protein

An expression vector is constructed so that the initiation codon (ATG: a sequence 78–80 in the base sequence shown in FIG. 2) in the insert DNA of the p4AF clone is located at a position of the 10th–15th base pair from a ribosome binding site of the expression vector pKK223-3 (manufactured by Pharmacia). Specifically, a deletion insert DNA wherein a sequence 0–77 of the base sequence shown in FIG. 2 has been deleted is prepared and inserted into a Sma I site of the pKK 223-3 vector. The resultant clone is inserted in *E. coli* JM109 and incubated while shaking at 37° C. for 12 hr in YT medium (a solution prepared by dissolving 16 g of bactotryptone, 10 g of yeast extract and 5 g of sodium chloride in distilled water to give a total volume of 1 liter) containing 100 μg/ml of ampicillin. Then, isopropylthiogalactoside is added thereto so as to have a concentration of 2 mM, and the mixture is further incubated while shaking at 37° C. for 5 hr. After the completion of the incubation, the medium is centrifuged at 10000 rpm for 10 min at a temperature of 15° C. to collect the resultant precipitate. Then, the precipitate is washed with a 30 mM Tris-HCl buffer (pH 7.5) containing 30 mM sodium chloride and suspended in the buffer. To 1 ml of the suspension are added 1 mg of lysozyme and 25 μl of 0.25M EDTA. The mixture is allowed to stand at room temperature for 15 min and subjected to freeze-thawing four times. Then, the melt is centrifuged at 10000 rpm for 60 min at a temperature of 4° C. to obtain a supernatant. An intended protein contained in the supernatant is identified by a method of Komada et al. (J. genVirol, 1989, vol. 70, pp. 3487–3492) and a method of Itoh et al. (Archives of Virology, 1987, vol. 95, pp. 211–224). After immune precipitation through the use of an anti-PIV-4A antibody, electrophoresis on a polyacrylamide gel is conducted to confirm that the gene expresses F protein in *E. coli*.

We claim:

1. An isolated DNA sequence consisting of the base sequence shown in SEQ ID NO. 1 or a base segment of at least 20 bases shown in SEQ ID NO. 1 that is specific for the identification of PIV-4A.

2. The DNA according to claim 1 wherein said base segment comprises at least 20 bases.

3. An isolated DNA sequence consisting of a base sequence which is complementary to the base sequence shown in SEQ ID NO. 1 or which is complementary to a base segment of at least 20 bases shown in SEQ ID NO. 1 that is specific for the identification of PIV-4A.

4. The DNA according to claim 3 wherein said base segment comprises at least 20 bases.

5. An isolated DNA sequence consisting of a base sequence corresponding to nucleotides 78–1706 shown in SEQ ID NO. 1.

6. An isolated DNA sequence consisting of a base sequence which is complementary to nucleotides 78–1706 shown in SEQ ID NO. 1.

7. An expression vector comprising the DNA sequence according to any one of claims 1, 2, 3, 4, 5 or 6.

8. A procaryotic or eucaryotic host cell transformed with the expression vector according to claim 7.

9. A diagnostic composition for determining the presence or absence of PIV-4A in a sample, consisting essentially of the DNA sequence of any one of claims 1, 2, 3, 4, 5 or 6 and a carrier thereof.

10. A diagnostic method for determining the presence or absence of PIV-4A in a sample, comprising:

reacting the sample with the DNA sequence according to any one of claims 1, 2, 3, 4, 5 or 6, and determining the occurrence of hybridization.

* * * * *